(12) United States Patent
Freeman et al.

(10) Patent No.: US 10,905,818 B2
(45) Date of Patent: Feb. 2, 2021

(54) BLOOD FILTERING OF INFLAMMATORY BIOMARKERS TO TREAT POST-RESUSCITATION SYNDROME

(71) Applicant: ZOLL Medical Corporation, Chelmsford, MA (US)

(72) Inventors: Gary Freeman, Newton Center, MA (US); Christopher Luke Kaufman, Somerville, MA (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 0 days.

(21) Appl. No.: 14/669,930

(22) Filed: Mar. 26, 2015

(65) Prior Publication Data

US 2015/0273129 A1    Oct. 1, 2015

Related U.S. Application Data

(60) Provisional application No. 61/972,827, filed on Mar. 31, 2014.

(51) Int. Cl.
*A61M 1/36* (2006.01)
*A61M 1/26* (2006.01)

(52) U.S. Cl.
CPC .......... *A61M 1/3633* (2013.01); *A61M 1/262* (2014.02); *A61M 1/3679* (2013.01); *A61M 1/3693* (2013.01); *A61M 2205/0238* (2013.01); *A61M 2205/33* (2013.01); *A61M 2205/505* (2013.01); *A61M 2205/70* (2013.01); *A61M 2205/75* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,033,881 A | * | 7/1977 | Pall | B01D 29/54 210/491 |
| 5,137,637 A | * | 8/1992 | Korin | B01D 63/16 210/321.67 |
| 5,362,406 A | | 11/1994 | Gsell et al. | |

(Continued)

FOREIGN PATENT DOCUMENTS

| | | |
|---|---|---|
| JP | 3881019 | 2/2007 |
| JP | 2011-024811 | 2/2011 |

(Continued)

OTHER PUBLICATIONS

Thermo Scientific. "Convert between times gravity and centrifuge rotor speed (RPM)". 2009.*

(Continued)

*Primary Examiner* — Ryan B Huang
(74) *Attorney, Agent, or Firm* — Greenblum & Bernstein, P.L.C.

(57) ABSTRACT

Provided is a therapeutic device that includes tubing; at least one pump; and a column or filter capable of removing leukocytes, cytokines, and/or other blood components from the blood of a patient to effectively treat or prevent post-resuscitation syndrome. Methods for treating and/or preventing post-resuscitation syndrome that include the use of such a device, or a filter or column capable of selectively removing inflammatory biomarkers, are also provided.

24 Claims, 9 Drawing Sheets

(56) References Cited

U.S. PATENT DOCUMENTS

| | | | |
|---|---|---|---|
| 5,571,418 | A | 11/1996 | Lee et al. |
| 5,879,316 | A | 3/1999 | Safar et al. |
| 5,997,496 | A | 12/1999 | Sekiguchi et al. |
| 6,659,289 | B1 | 12/2003 | Masuko et al. |
| 7,641,794 | B2 | 1/2010 | Oka et al. |
| 7,655,146 | B2 | 2/2010 | Ozeki et al. |
| 8,038,638 | B2 | 10/2011 | Roberts et al. |
| 8,496,833 | B2 | 7/2013 | Kobayashi |
| 2005/0277863 | A1* | 12/2005 | Davidner .............. A61L 2/0011 604/5.01 |
| 2010/0217172 | A1* | 8/2010 | Hyde .................. A61M 1/3681 604/5.01 |
| 2012/0265116 | A1 | 10/2012 | Szamosfalvi et al. |
| 2012/0302995 | A1* | 11/2012 | Hochareon ......... A61M 1/3613 604/508 |
| 2013/0261529 | A1 | 10/2013 | O'Mahony |

FOREIGN PATENT DOCUMENTS

| | | |
|---|---|---|
| JP | 2012-213635 | 11/2012 |
| WO | 99/44710 | 9/1999 |

OTHER PUBLICATIONS

Crichton et al. "Iron transport and storage". Eur. J. Biochem. 1987, 164, p. 485-506. (Year: 1987).*

Löfås et al., "A Novel Hydrogel Matrix on Gold Surfaces in Surface Plasmon Resonance Sensors for Fast and Efficient Covalent Immobilization of Ligands" *J. Chem. Soc., Chem. Commun.* 21:1526-28, 1990.

Yang et al., "Detection of Picomolar Levels of Interleukin-8 in Human Saliva by SPR" *Lab Chip* 5:1017-23, 2005.

Adrie et al., "Successful Cardiopulmonary Resuscitation After Cardiac Arrest as a 'Sepsis-Like' Syndrome" *Circulation* 106:562-68, published online Jul. 8, 2002.

Adrie et al., "Postresuscitation Disease After Cardiac Arrest: A Sepsis-Like Syndrome?" *Curr. Opin. Crit. Care* 10:208-12, 2004.

Laurent et al., "High-Volume Hemofiltration After Out-of-Hospital Cardiac Arrest," *J. Am. Coll. Cardiol.* 46(3):432-37, 2005.

Nolan et al., "Post-Cardiac Arrest Syndrome: Epidemiology, Pathophysiology, Treatment, and Prognostication a Scientific Statement from the International Liaison Committee on Resuscitation; the American Heart Association Emergency Cardiovascular Care Committee; the Council on Cardiovascular Surgery and Anesthesia; the Council on Cardiopulmonary, Perioperative, and Critical Care; the Council on Clinical Cardiology; the Council on Stroke" *Resuscitation* 79:350-79, 2008.

Sipos et al., "Changes in Interleukin-10 mRNA Expression Are Predictive for 9-Day Survival of Pigs in an Emergency Preservation and Resuscitation Model" *Resuscitation* 81:603-08, 2010.

Rich et al., "BIACORE J: A New Platform for Routine Biomolecular Interaction Analysis" *Journal of Molecular Recognition* 14:223-28, 2001.

Bruil et al., "The Mechanisms of Leukocyte Removal by Filtration" *Transfusion Medicine Reviews*, IX(2):145-66, 1995.

Plasauto-Sigma Catalogue, Asahi Kasei Kuraray Medical Co., Ltd.; pp. 1-10, 2011.

Peberdy et al. "Initial Cytokine Levels are Associated with Outcome after Cardiac Arrest," poster presentation, AHA Resuscitation Science Symposium, Nov. 2013.

Samborska-Sablik et al., "The Role of the Immuno-Inflammatory Response in Patients after Cardiac Arrest" *Arch. Med. Sci.* 4:619-26, 2011.

Myszka et al. "Kinetic Analysis of Ligand Binding to Interleukin-2 Receptor Complexes Created on an Optical Biosensor Surface" *Protein Science* 5:2468-78, 1996.

Kim et al., "Effect of Prehospital Induction of Mild Hypothermia on Survival and Neurological Status Among Adults with Cardiac Arrest a Randomized Clinical Trial" *JAMA*, pp. E1-E8, published online Nov. 17, 2013.

Cellsorba EX Leukocytapheresis Column product sheet (2 pages), Oct. 2010.

Official Communication from the ISA issued for patent family member PCT/US2015/022764, dated Jun. 18, 2015.

Lipton, "Ischemic Cell Death in Brain Neurons" *Physiological Reviews* 79(4):1431-1568, 1999.

Hidaka et al., "Dynamic Changes in Cytokine Levels in Serum and Synovial Fluid Following Filtration Leukocytapheresis Therapy in Patients with Rheumatoid Arthritis" *Journal of Clinical Apheresis* 16:74-81, 2001.

Allary et al. "Glucocorticoids and Sepsis" Minerva Anestesiol. 71(12):759-68, 2005.

Tsai et al., "The Effect of Hydrocortisone on the Outcome of Out-of-Hospital Cardiac Arrest Patients: A Pilot Study" *American Journal of Emergency Medicine* 25:318-25, 2007.

Mackenzie et al., "Intracellular Iron Transport and Storage: From Molecular Mechanisms to Health Implications" *Antioxidants & Redox Signaling* 10(6):997-1030, 2008.

He et al., "Peripheral Leukocytapheresis Attenuates Acute Lung Injury Induced by Lipopolysaccharide In Vivo" *Mediators of Inflammation* 2012:1-9, 2012.

Crow et al., "The Mitochondrial Death Pathway and Cardiac Myocyte Apoptosis" *Circ. Res.* 95:957-70, 2004.

International Search Report and Written Opinion of the International Search Authority issued in PCT/US2015/022764, dated Sep. 3, 2015.

Notice of Reasons for Rejection issued in JP Patent Application No. 2016-557644, dated Dec. 4, 2018, along with an English-language translation.

Decision of Rejection issued in JP Patent Application No. 2016-557644, dated Nov. 5, 2019, along with a machine English-language translation.

\* cited by examiner

BLOOD FILTERING OF INFLAMMATORY BIOMARKERS TO TREAT POST-RESUSCITATION SYNDROME

CROSS-REFERENCE TO RELATED APPLICATION

This present application claims the benefit under 35 U.S.C. § 119(e) of U.S. Provisional Application No. 61/972,827, filed Mar. 31, 2014, the disclosure of which is hereby expressly incorporated by reference herein in its entirety.

BACKGROUND OF THE INVENTION

1. Field of the Invention

The invention relates to methods of treating or preventing post-resuscitation syndrome (PRS) comprising filtering or removing inflammatory biomarkers and/or other blood components from a subject. The invention also relates to a therapeutic device for treating post-resuscitation syndrome.

2. Background of the Invention

Post-resuscitation syndrome (PRS) describes a complex cascade of physiologic events following a cardiac arrest and/or other loss of circulation that remains difficult to treat. PRS shares much in common with the classic condition of sepsis. PRS is characterized by hyperthermia, hypotension, and multiple organ failure (Laurent, J. Am. Coll. Cardiol. 46(3):432-37, 2005, which is incorporated by reference herein in its entirety). PRS is also known as post-cardiac arrest syndrome because the term post-resuscitation implies that the act of resuscitation is complete (Nolan et al., Resuscitation 79:350-379, 2008, which is incorporated by reference herein in its entirety). However, the more complex phase of resuscitation begins after patients regain spontaneous circulation. Id.

PRS includes the following pathophysiological processes: (1) post-cardiac arrest brain injury, (2) post-cardiac arrest myocardial dysfunction, and (3) systemic ischemia/reperfusion response. (Nolan et al., Resuscitation 79:350-379, 2008). Of course, the syndrome is generally further complicated by the original pathological factors that lead to the initiating cardiac arrest (Nolan et al., Resuscitation 79:350-379, 2008).

Post-cardiac arrest brain injury may result in impaired cerebrovascular autoregulation, cerebral edema, and/or post-ischemic neurodegeneration. Clinical manifestations include coma, seizures, myoclonus, cognitive dysfunction, persistent vegetative state, secondary Parkinsonism, cortical stroke, spinal stroke, and brain death (Nolan et al., Resuscitation 79:350-379, 2008).

Post-cardiac arrest myocardial dysfunction may result in global hypokinesis (myocardial stunning), reduced cardiac output, and acute coronary syndrome. Clinical manifestations include early revascularization of acute myocardial infarction, hypotension, dysrhythmias, and cardiovascular collapse (Nolan et al., Resuscitation 79:350-379, 2008).

Systemic ischemia/reperfusion response may result in systemic inflammatory response syndrome, impaired vasoregulation, increased coagulation and/or coagulation abnormalities, adrenal suppression and/or dysfunction, impaired tissue oxygen delivery and utilization, and impaired resistance to infection. Clinical manifestations include ongoing tissue hypoxia/ischemia, hypotension, cardiovascular collapse, pyrexia (fever), hyperglycemia, multi-organ failure, and infection (Nolan et al., Resuscitation 79:350-379, 2008).

PRS has also been associated with complement activation, improper regulation of cytokine production by leukocytes, expression of adhesion molecules, cytokine release, and endotoxin presence in plasma (Laurent et al., J. Am. Coll. Cardiol. 46(3):432-37, 2005; and Adrie et al., Curr. Opin. Crit. Care 10:208-212, 2004, which is incorporated herein by reference in its entirety).

There is a high mortality rate for patients who initially achieve return of spontaneous circulation, which mortality rate is attributed to a pathophysiological response involving the immune system and multiple organs (Nolan et al., Resuscitation 79:350-379, 2008). Indeed, PRS is characterized by a large inflammatory response that has been linked to increased oxidative stress which can lead to nerve cell malfunction or death and subsequently poor outcomes for patients.

For example, the release of oxygen free radicals, coagulation factors, complement-activation products, and cytokines may occur during revascularization after ischemia (reperfusion syndrome). Previous studies have shown that non-survivors of cardiac arrest have a significantly greater escalation of these pro-inflammatory biomarkers as compared to survivors (Adrie et al., Circulation 106:562-568, 2002; Sipos et al., Resuscitation 81:603-608, 2010, which documents are incorporated by reference herein in their entireties). Moreover, the release of these factors leads to marked activation of neutrophils with up-regulation of their surface adhesion molecules (Adrie et al., Curr. Opin. Crit. Care 10:208-212, 2004). The resulting leukocyte adhesion is an important step in vascular endothelium injury, leading to increased microvascular permeability and thrombosis. Id. The elevation of circulating pro-inflammatory as well as immunomodulatory cytokines and adhesion molecules is a feature of PRS, which mimics the immunological disorders observed in sepsis.

PRS treatment is time sensitive, and care of PRS patients must accommodate a range of patients, for example, patients who are hemodynamically stable as well as unstable and/or comatose patients. The phases of PRS/post-cardiac arrest syndrome may be categorized as set forth in the following table:

TABLE 1

Phases of Post-Cardiac Arrest Syndrome*

| Phase | Description |
| --- | --- |
| Immediate | 0-20 min within the return of spontaneous circulation (ROSC) |
| Early | 20 min to 6-12 h |
| Intermediate | 6-12 h to 72 h |
| Recovery | 72 h to disposition |
| Rehabilitation | post-disposition |

*Source: Nolan et al., Resuscitation 79: 350-379, 2008.

Others have noted that within the first 24 hours after the cardiac arrest or ischemic event, multifocal hypoxia leads to microcirculatory dysfunction, resulting in rapid release of toxic enzymes and free radicals into the blood (Adrie et al., Circulation 106:562-568, 2002). Over the next 1 to 3 days, cardiac function and systemic function improve, but intestinal permeability also increases, which may lead to sepsis and/or multiple organ dysfunction. Id. Days after cardiac arrest serious infection may occur and/or the patient may decline rapidly and die. Id.

Therapeutic hypothermia after ventricular fibrillation cardiac arrest improves neurologic outcome and has been recommended for post-resuscitation care. Therapeutic hypothermia was thought to benefit patients because the cooling of the body would reduce the amount of the pro-inflammatory substances circulating in the cardiovascular system. However, a recent study in a pig model of cardiac arrest with hypothermia indicates that the inflammatory response still occurs (with corresponding upregulation of markers of systemic inflammation) even when the animals were cooled as early as possible during the arrest (Sipos et al., *Resuscitation* 81:603-608, 2010).

Sharp rises in various cytokines and soluble receptors occur in the bloodstream as early as 3 hours after cardiac arrest. Several cytokines, including IL-6, show greater elevation in nonsurvivors than in survivors as well as in patients requiring vasopressor therapy compared with other patients (Adrie et al., *Curr. Opin. Crit. Care* 10:208-212, 2004).

However, cytokines and other blood components may be difficult to remove from the blood, especially in a short period of time following loss of circulation/cardiac arrest. For example, cytokines and other toxins are often bound to the blood protein albumin, and conventional dialysis membranes do not remove substantial quantities of these protein-bound toxins from the blood. This is because protein-impermeable membranes are generally used in dialysis methods. Consequently, extracorporeal circuits such as continuous renal replacement therapies (CRRT), coupled plasma filtration adsorption (CPFA) and continuous veno-venous hemodiafiltration (CVVHDF) have been developed to minimize cell-associated cytokine concentrations in the blood of septic patients. However, most extracorporeal circuits to date function primarily as artificial kidneys or perfusion devices.

There remains a need for treatment methods that filter harmful substances from the blood of a subject post-cardiac arrest and for methods of treating or preventing PRS in subjects having, or at risk of having, PRS. There also remains a need for a device capable of selectively removing blood components for the effective prevention and/or treatment of PRS.

SUMMARY OF THE INVENTION

Accordingly, there is provided a therapeutic device comprising tubing; at least one pump; and a column or filter configured to selectively remove leukocytes, cytokines, and/or other blood components from the blood of a patient having or at recognized risk of having PRS at a blood flow rate through the filter or column of at least 2.5 L per hour to effectively treat or prevent PRS. The therapeutic device may optionally comprise a blood temperature regulator.

There is also provided such a device comprising a column or filter that is capable of removing interleukins, tumor necrosis factor α (TNF-α), c-reactive protein (CRP), nuclear factor-kappa B (NF-κB) subunit p65, interferon-γ, elastase, inducible NO synthase, heme oxygenase-1, free radicals, intracellular adhesion molecules, vascular cell adhesion molecule-1, complement components, granulocyte-macrophage colony-stimulating factor (GM-CSF), monocyte chemoattractant protein-1 (MCP-1), Regulated on Activation, Normal T Cell Expressed and Secreted (RANTES) protein, and/or von Willibrand factor (VWF). The interleukins include, for example, IL-1β, IL-2, IL-4, IL-6, IL-10, and IL-15. The intracellular adhesion molecules include ICAM1, ICAM2, ICAM3, ICAM4, and ICAM5. The free radicals are not limited and may be, for example, free iron radicals or free oxygen radicals. The complement components include, for example, C3a and terminal complement complex (TCC).

In an embodiment, the device may selectively remove IL-6.

In an embodiment, the device may be portable.

In an embodiment, the device may be configured for a blood filtration rate of 2.5-5 L/hr.

There is also provided a device as described above, wherein the filter or column comprises a hydrogel layer to which one or more molecules capable of selectively binding leukocytes, cytokines, and/or other blood components has been immobilized. In an embodiment, the hydrogel comprises dextran.

The invention also provides a therapeutic device as described above which comprises a surface treatment filter.

There is also provided a therapeutic device comprising tubing, at least one pump, a blood temperature regulator, and a column or filter, wherein the device is capable of detecting the presence and/or amount of soluble PRS-inducing or -exacerbating blood components, and selectively removing or partially removing one or more of the detected blood components from the blood of a subject.

The invention also provides such a device further comprising one or more of an air-free pressure chamber, a pressure sensor, an oxygenator, a blood leak detector, an air detector, a cooler, a heater, an LED touch screen, and/or a battery.

In an embodiment, the LED touch screen displays information relating to the nature and/or amount of one or more PRS-inducing or -exacerbating blood components in the blood to be filtered. For example, the LED touch screen may display information relating to IL-6 plasma concentration levels. The device may also be configured to detect and display information about the nature and/or amount of the one or more PRS-inducing or -exacerbating blood components in the blood to be filtered within about 45 minutes or less after filtration has started. The device may also be configured to detect and display information about the nature and/or amount of the one or more PRS-inducing or -exacerbating blood components in the blood to be filtered in 30 minute intervals and to adjust flow rate through the filter or column based on the information.

In an embodiment, the device may be configured to increase flow rate through the filter or column when IL-6 plasma concentration levels are detected above 200 μg/L after 45-75 minutes after filtering with the device.

There is also provided such a device in which the LED touch screen displays information relating to the nature and/or amount of one or more PRS-inducing or -exacerbating blood components in the blood post-filtration.

There is also provided a device as described above, which adjusts flow rate through the filter or column to maintain IL-6 plasma concentration levels below 200 μg/L in post-filtration blood.

In an embodiment, the therapeutic device of the present invention may be configured to induce therapeutic hypothermia in the subject.

The device of the present invention may also be configured for automated plasma recovery and pressure-driven automatic flow control.

In an embodiment, the filter or column may be present as part of a detachable filtration module. The detachable module may be exchanged or selected for insertion in the device depending upon the blood component or blood components to be removed.

In another aspect, there is also provided a therapeutic device for filtering blood comprising a pump, and a filtering module comprising one or more cylinders and filter material on at least a partial inner surface of the one or more cylinders, the therapeutic device being configured to send blood into and/or through the one or more cylinders along a spiral path such that blood components that induce or exacerbate PRS in a subject, or a portion thereof, are selectively retained in the one or more cylinders. Such a device, may for example, slowly inject blood in an upward direction combined with a fast rotary motion to exert a centrifugal force on the blood sent into and/or through the one or more cylinders, such that one or more of the blood components that induce or exacerbate PRS in a subject contact the filter material. In an embodiment, the therapeutic device may be configured to obtain a centrifugal force within the one or more cylinders of 10,000 to 100,000 G.

In another system, biocompound-specific adhesion is used to filter the blood, rather than a size-based pore filtration. In one embodiment, a spiral-wound filter is constructed to provide a compact filter with a large surface area over which the blood is flowed. The filter is made up of an outer housing in which the blood is contained, composed of a cylinder side wall and two end caps (FIG. 5A). Inside the housing is the filter element (FIG. 5B), whose filter inlet port and exhaust port protrude through the walls of the end caps via sealed holes. The blood flows in a spiral fashion from the fluid inlet port into the inner tube then into the spiral space via the inlet exhaust ports. The blood flows in a spiral fashion within the spiral space and because of the spiral shape, the blood is exposed to a very large surface area. So, for instance, for a filter diameter of 6 inches and a length of 6 inches and a spacing between the layers in the spiral of 0.2 inches, the surface area of blood/filter contact is 900 square inches. The filter element is a laminate structure of a substantially impermeable, flexible but semi-rigid substrate support layer, of a relatively blood-inert composition such as polyethylene or cellulose. Laminated to that surface is the active surface matrix, in some cases made of carboxymethyl dextran to which molecules can be covalently attached using well-defined chemistries (see Lofas S, Johnsson B, *J. Chem. Soc. Chem. Commun.* 21:1526-1528, 1990). The dextran layer creates a suspended hydrogel that is conducive to adhering blood agents. In general, the carboxymethyl dextran minimizes nonspecific binding of biomolecules to the surface and increases the binding capacity of the surface. The surface chemistry of the dextran may be modified to provide a surface with altered properties such as hydrophobic, lipophylic, or lower charge.

A pliant over-molded sealing and spacing ridge is over-molded onto the perimeter of the laminate structure such that when it is wound around the inner tube, it provides multiple sealing functions: 1) it seals against the inner tube; 2) it seals against the adjoining layers at the two ends so that blood fluid is forced to flow only spirally; 3) it seals against the outer tube; and when the filter element is placed into the cylinder side wall and the two end caps are placed and compressed into position before being glued or ultrasonically welded to the cylinder side wall, they seal against the end caps and side wall.

As described, for instance, in Yang et al., *Lab Chip* 5:1017-1023, 2005, the surface is functionalized to adhere to PRS-inducing or -exacerbating blood components. For instance, for IL-8 specific adhesion, "two monoclonal antibodies recognizing different epitopes of IL-8" may be used. "MAB208 is a mouse immunoglobulin $G_1$ ($IgG_1$) that was raised against human IL-8 and then protein G column purified from mouse ascites fluid by R & D Systems (Clone No. 6217.111; Cat. No. MAB208). JK8-2 is a mouse IgG1 that was raised against human IL-8 and produced by Biolegend (San Diego, Calif.; Clone No. JK8-2; Cat. No. 508502). It was purified by protein G affinity chromatography and then biotinylated. As a polishing step, size-exclusion chromatography (Amersham FPLC with a Superdex-200 gel filtration column) was applied by our laboratory to eliminate traces of other proteins such as albumin from both monoclonal antibodies. The antibody fractions were collected in HBS-EP buffer and concentrated with Amicon Ultra Centrifugal Filter Devices (10 kDa) from Millipore (Billerica, Mass.; Product No. UFC901024). The purity was determined by SDS-PAGE and MALDI-TOF mass spectroscopy. The concentrations were measured using a Micro BCA Protein Assay Kit from Pierce (Rockford, Ill.; Cat. No. 23235)." Id. Other monoclonal antibodies may be used to bind to one or more of these PRS-inducing or -exacerbating blood components.

Alternatively, the surface matrix may be functionalized to adhere to free iron in the bloodstream. Free iron, typically in the form of $Fe^{3+}$, can be captured by iron-binding compounds such as siderophores that may be used to functionalize the surface of the surface matrix. Siderophores are iron-complexing compounds of low molecular weight that are synthesized by bacteria and fungi, and serve to deliver the iron to the microbes. Ferriooxamine is one example. Siderophores are classified into five principal groups according to their chemical structures: hydroxamates, catecholates, carboxylates, heterocyclic compounds, and mixed types. All the natural siderophores are designed to chelate (adhere to) Fe(III) selectively (Reference: Inorganic Biochemistry of Iron Metábolism, Robert Crichton, 2001, Wiley and Sons).

The blood is circulated in the spiral fashion in the spiral space of the filter element, flowing outwardly until it reaches the exit intake ports of the outer tube, through which the blood exits into the outer tube and finally out the exhaust port. The device may employ pressure at the inlet port as well as negative pressures at the exhaust port. The filter may be alternatively configured to have the blood flow spirally inward toward the central tube, in which case the center tube becomes the exhaust port and the outer tube becomes the intake port. The surface matrix may be composed of alternative materials such as spun polyethylene teraphthalate (PET), cellulose acetate, polyurethanes, nylon, polyacrylonitrile or polypropylene.

The semi-rigid substrate may be formed into the cylindrical spiral shape by creating features on the inner tube that the over-molded ridge to which the in-most edge of the semi-rigid substrate is affixed and then winding the semi-rigid substrate around the inner tube as a mandrel. The semi-rigid material may be a polymer that can be thermo-formed and the material can be heated to soften it while the winding is occurring. The inner mating surface of the end caps into which the filter element seats may be conically shaped so that when all the components are pressed together for the final assembly, the inner wall of the end caps press inward on the over-molded sealing edge at the top and bottom of the filter element, thus sealing the end-surfaces of the filter element. In order to improve sealing, the ends of the filter element may also be sealed with a non-bioactive sealing agent like silicone.

The flexible semi-rigid support layer should have both a smooth surface and preferably a surface that may be treated with a material of low binding force to the blood so that it is conducive for maximal laminar flow along the surface of the semi-rigid support layer. On the other hand, the surface matrix will be roughened which will result in turbulent, non-laminar flow along its surface. These two surface properties will result in the blood having different velocities relative to the inner and outer regions of the blood volume.

This differential velocity will cause a rolling-mixing action of the blood volume, thereby causing enhanced contact of all the blood volume with the activated surface matrix, and further enhancing the removal of the agents.

There is also provided a filter or column comprising a filter material capable of removing leukocytes and/or soluble blood components from the blood of a subject having or at recognized risk of having PRS at a blood flow rate through the filter of at least 2.5 L per hour to effectively treat or prevent PRS. The filter or column may selectively remove cytokines from the blood.

There is also provided a system for determining a treatment procedure for a subject having or at recognized risk of having PRS comprising a module for obtaining a blood sample from the subject; a module for measuring and/or identifying the presence, absence, or amount of one or more biomarkers present in the blood of the subject after cardiac arrest, ischemia or other loss of circulation; a module and LED screen capable of determining and displaying a treatment procedure for the subject based on the presence, absence, or amount of the measured and/or identified one or more biomarkers; and an adjustable filter module.

The present invention also provides a method of treating or preventing PRS comprising filtering blood of a subject having or at recognized risk of having PRS with a device a described above.

There is also provided a method of treating or preventing PRS comprising passing the blood of a subject at risk of PRS through a device configured to remove leukocytes, cytokines, free radicals, von Willibrand factor, and/or other blood components at a flow rate of at least 2.5 L per hour to effectively treat or prevent PRS. In an embodiment, there is also provided such a method wherein an anticoagulant, a chelating agent, and/or a glucocorticoid is added to the blood as it passes through the device. The anticoagulant may be Anticoagulant Citrate Dextrose Solution A (ACD-A) or heparin. There is also provided such a method, wherein the device is configured for extracorporeal blood circulation. For example, the method may comprise filtering the blood extracorporeally to remove leukocytes. The leukocytes to be removed may be lymphocytes, granulocytes and/or monocytes. In an embodiment, the method comprises partial removal of peripheral neutrophils.

There is also provided a method of treating or preventing PRS comprising inducing hypothermia in a subject at risk of PRS, and passing blood of a subject at risk of PRS through a device as described above.

In an embodiment, there is also provided a cylindrical filter element comprising a surface activated fiber sheet and a substrate support that form a layer, the layer wound in a spiral about an inner tube; and a space adjacent to at least a partial surface of the fiber sheet, the filter element being configured to accommodate blood flow in a spiral path and to allow blood to come into contact with the fiber sheet such that blood components that induce or exacerbate PRS in a subject, or a portion thereof, are selectively retained in the filter element. In an embodiment, such a cylindrical filter element may comprise a flexible semi-rigid support layer having a smooth surface and a surface treated with a material of low binding force in the blood. In an embodiment, such a cylindrical filter element may comprise a roughened surface matrix for turbulent, non-laminar flow along its surface.

In an embodiment, there is provided a therapeutic device comprising a filter element comprising a surface activated filtering agent that attracts free iron, and which is configured to selectively remove the free iron from the blood of a patient having or at recognized risk of having PRS at a blood flow rate through the filter element of at least 2.5 L per hour to effectively treat or prevent PRS.

In an embodiment, there is provided a filter element comprising a filter material having an enhanced surface area for efficient and selective removal of one or more PRS-inducing or -exacerbating blood components from the blood of a patient having or at recognized risk of having PRS at a blood flow rate through the filter element of at least 2.5 L per hour to effectively treat or prevent PRS. In an embodiment, the filter element may comprise carbon nanofibers or sintered nanoparticles. In an embodiment, the surface area of the filter material may be enhanced by chemical vapor deposition.

In another embodiment, there is provided a method of making a filter element with an enhanced surface area, the method comprising obtaining a filter material capable of removing leukocytes and/or soluble blood components from the blood of a subject having or at recognized risk of having PRS at a blood flow rate through the filter element of at least 2.5 L per hour to effectively treat or prevent PRS, and coupling nanofibers to the filter material or sintering nanoparticles to the filter material.

In another embodiment, there is provided a method of making a filter element with an enhanced surface area, the method comprising obtaining a filter material capable of removing leukocytes and/or soluble blood components from the blood of a subject having or at recognized risk of having PRS at a blood flow rate through the filter element of at least 2.5 L per hour to effectively treat or prevent PRS, and exposing the filter material to chemical vapor deposition.

DETAILED DESCRIPTION OF THE INVENTION

Figure 1:
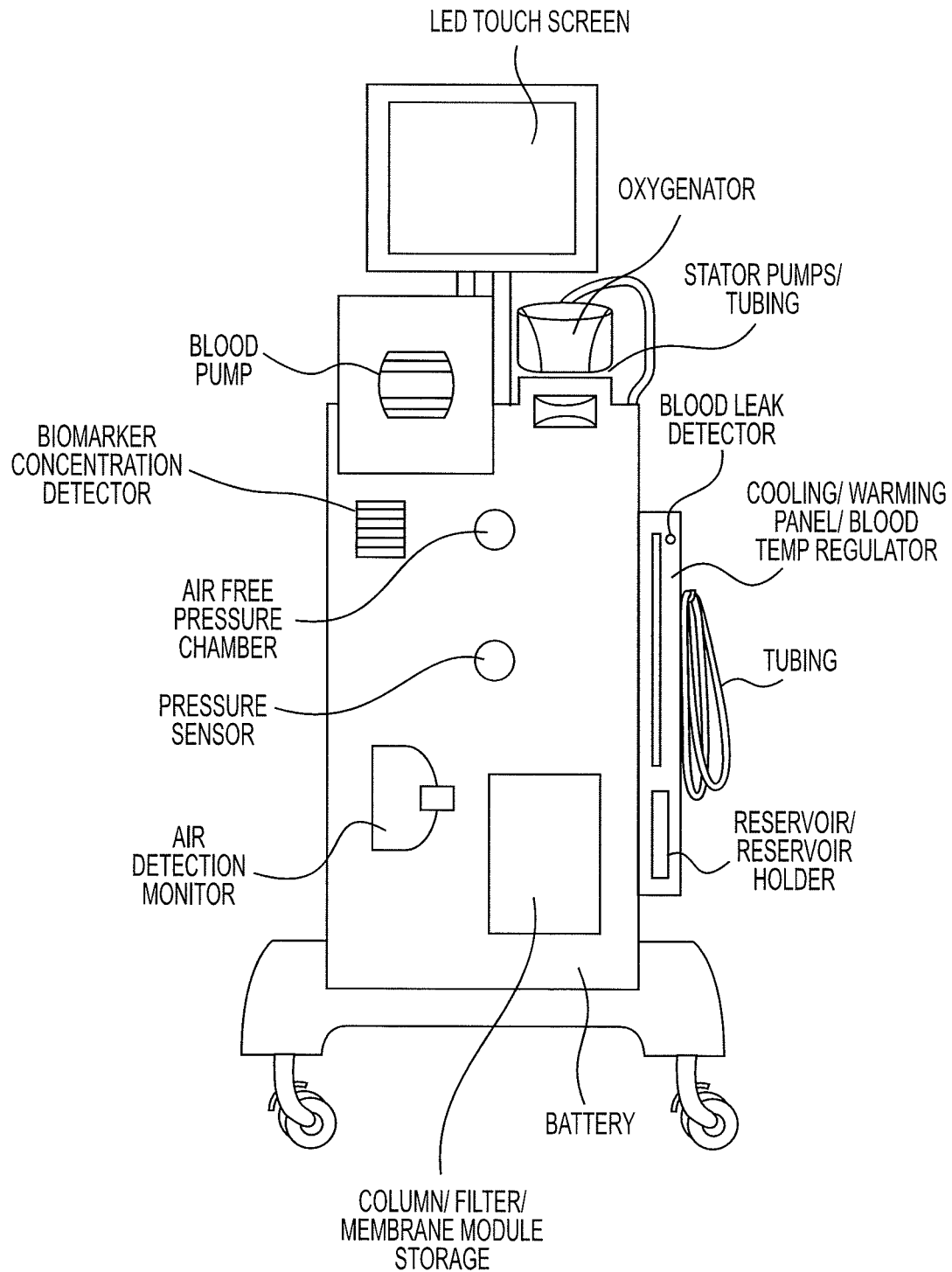
FIG. 1 shows a portable device capable of removing leukocytes, cytokines, and/or other blood components from the blood of a patient to effectively treat post-resuscitation syndrome.
Figure 2:
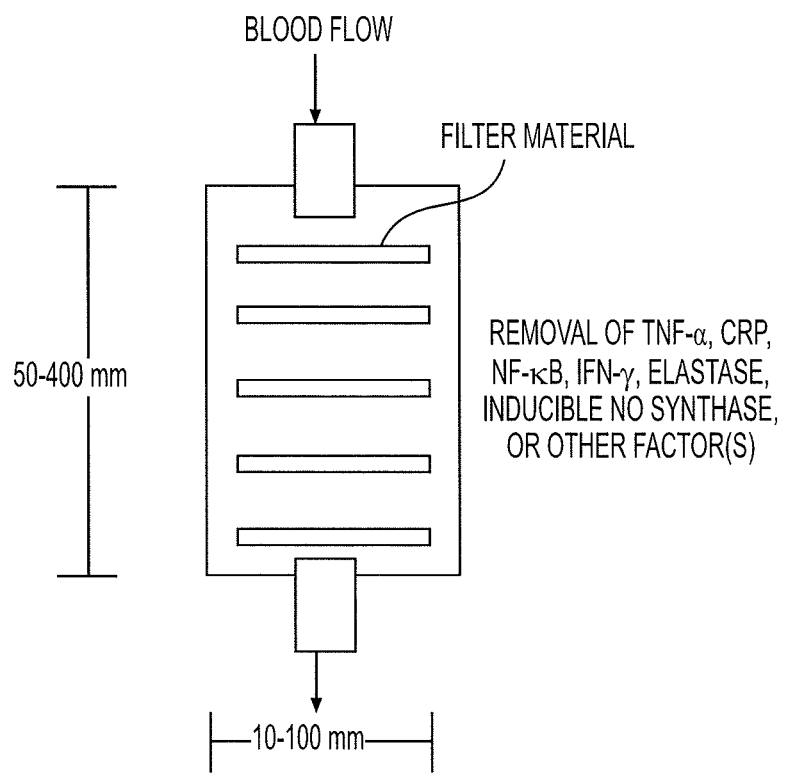
FIG. 2 shows a cylindrical column for filtering blood of a subject that has or is at risk of having post-resuscitation syndrome.
Figure 3B:
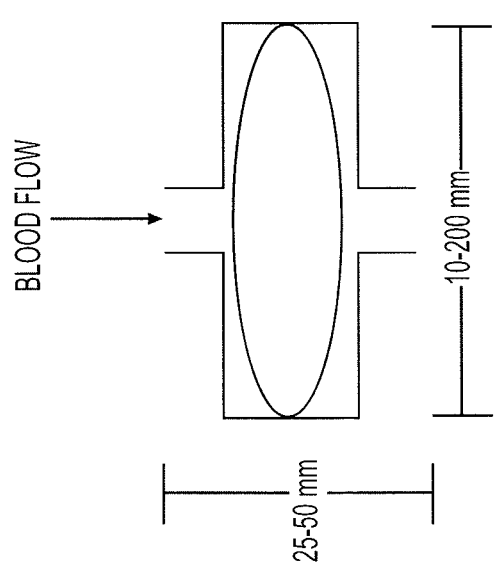
FIG. 3B shows three possible membranes that may be included in the filter module for removing one or more types of cells and/or other blood components.
Figure 3A:
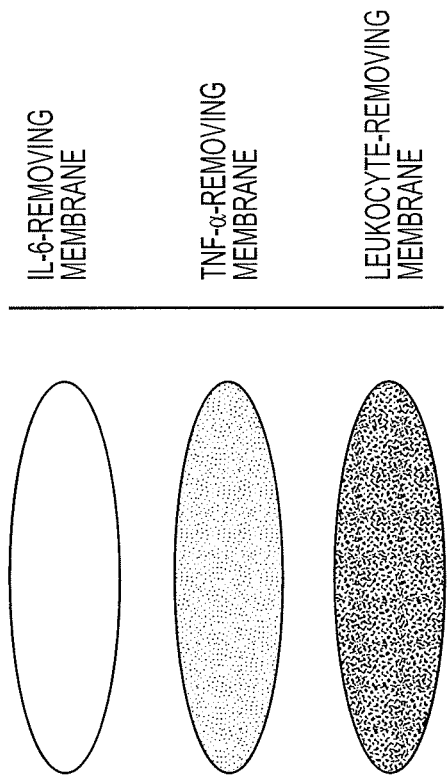
FIG. 3A shows a filter module for filtering blood of a subject that has or is at risk of having post-resuscitation syndrome.
Figure 4A:
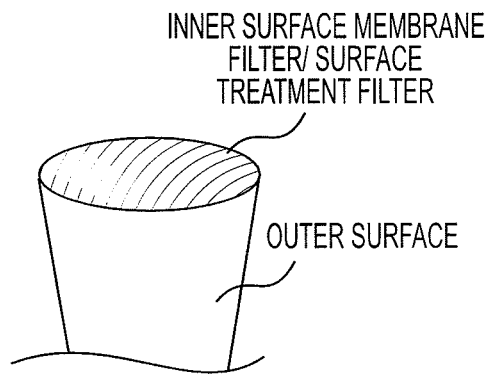
FIG. 4A provides a partial view of a conical-shaped cylinder having an inner surface comprising a membrane filter or surface treatment filter.
Figure 4B:
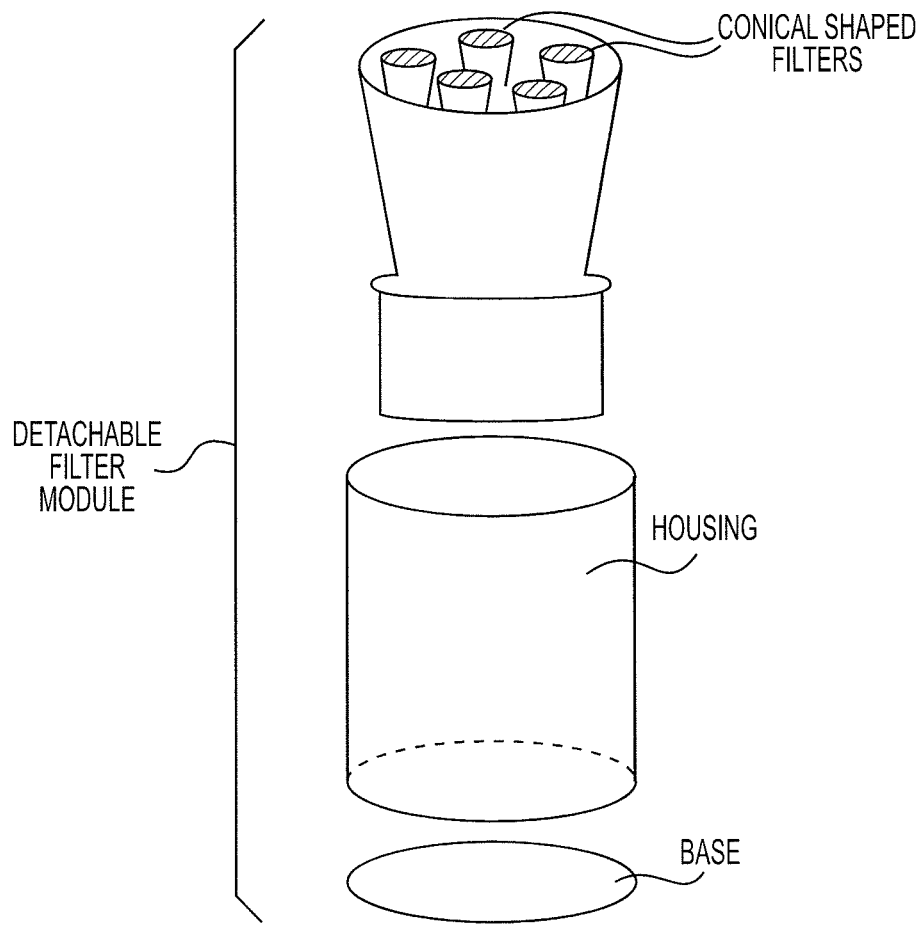
FIG. 4B shows a detachable filter module comprising multiple conical-shaped filters, housing for the filters, and a base.
Figure 5A:
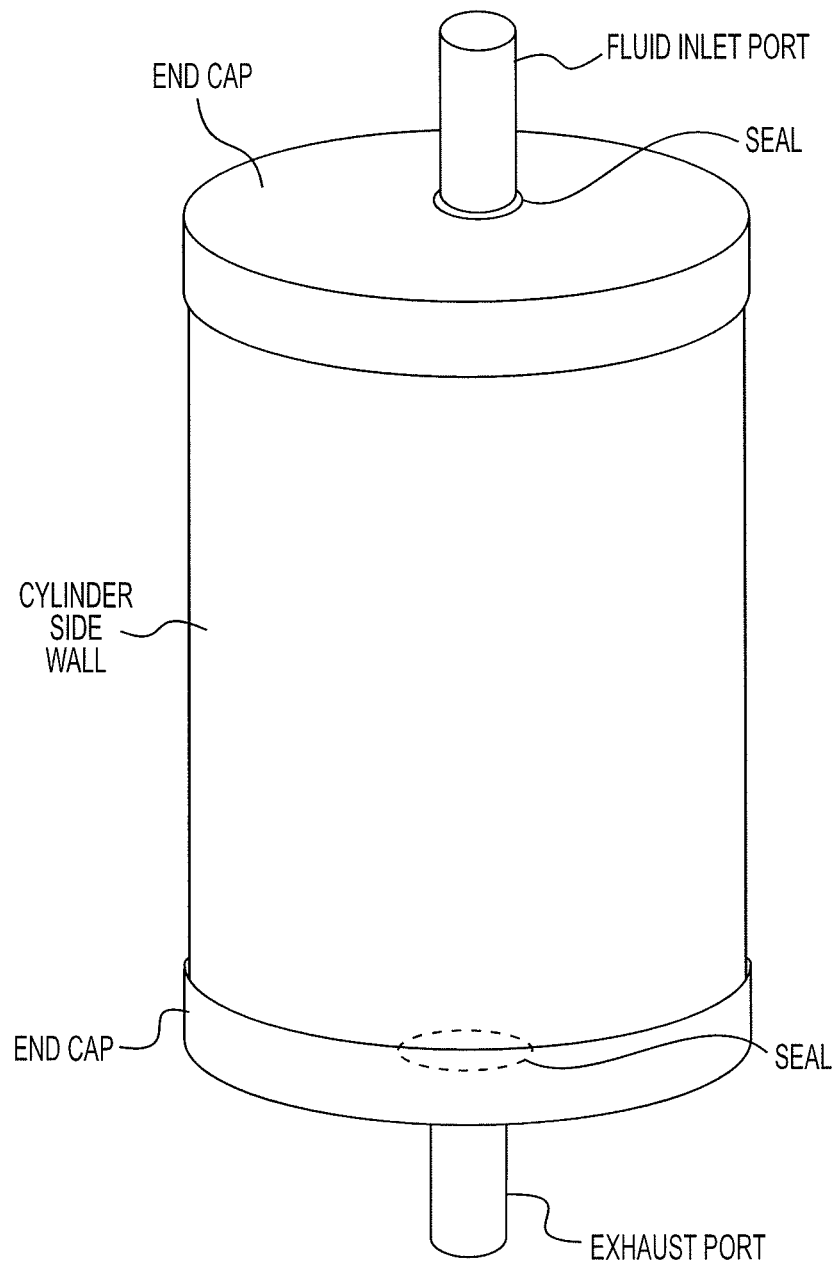
FIG. 5A shows the outer housing for a filter element.
Figure 5B:
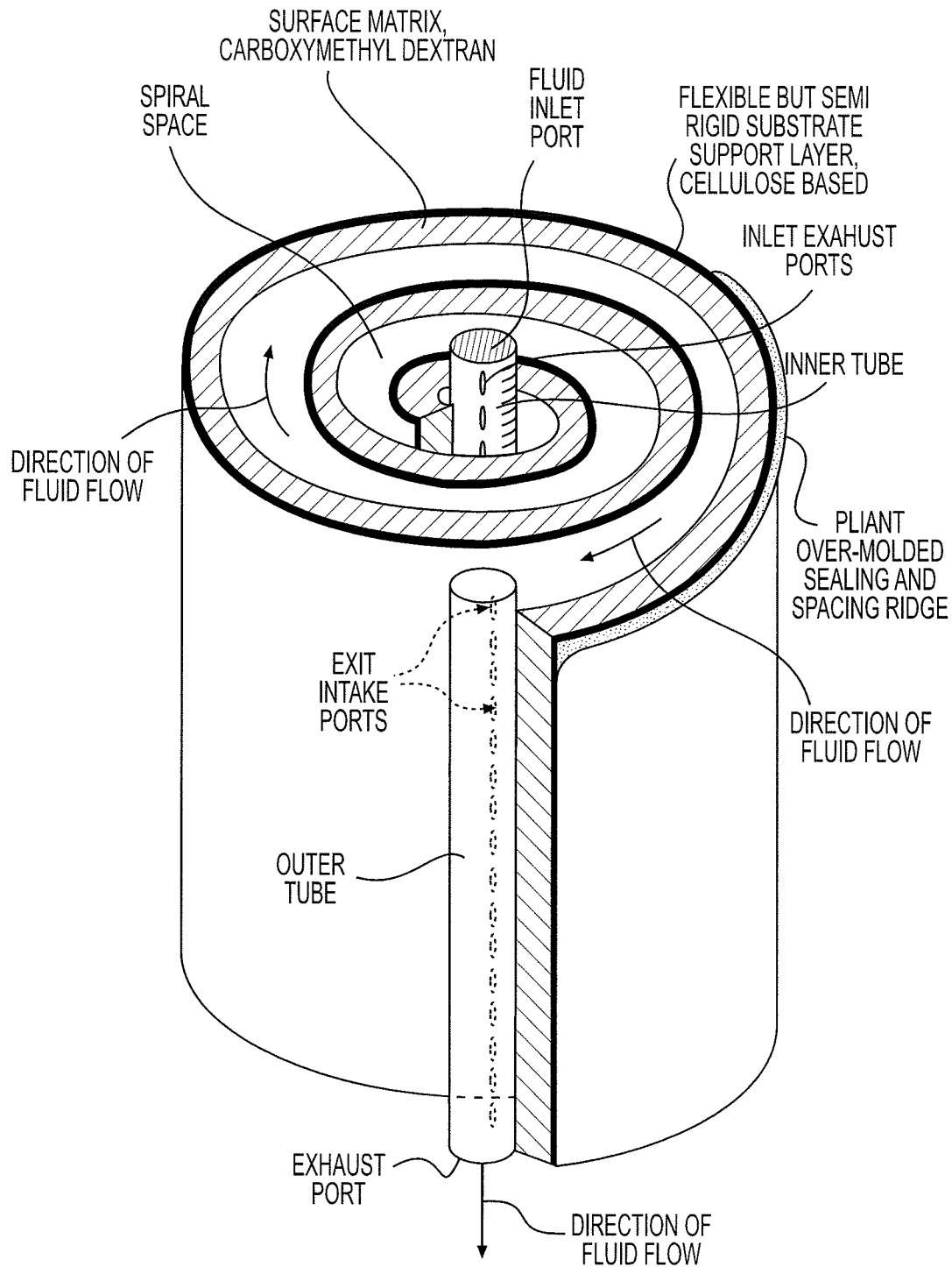
FIG. 5B shows a filter element, which may be placed in an outer housing.
Figure 6:
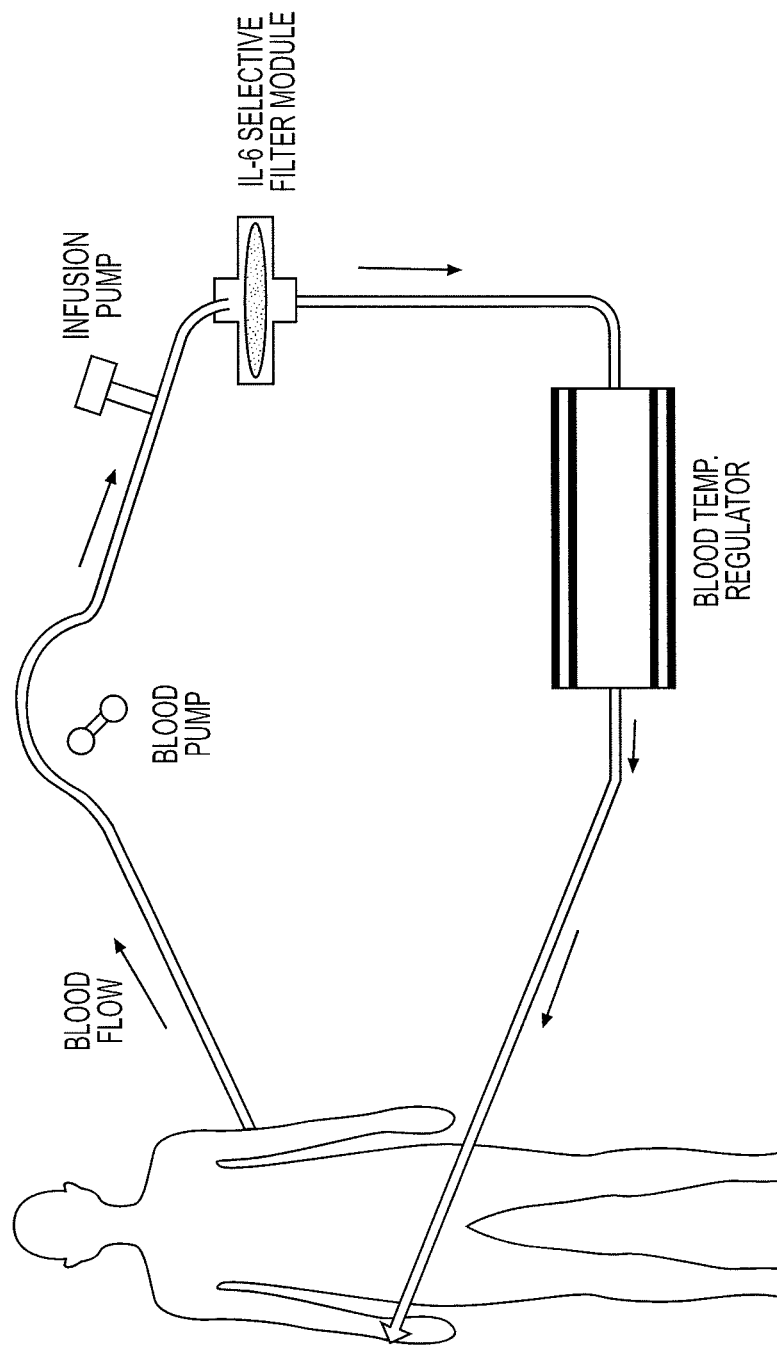
FIG. 6 shows extracorporeal filtration of IL-6 from a subject.
Figure 7:
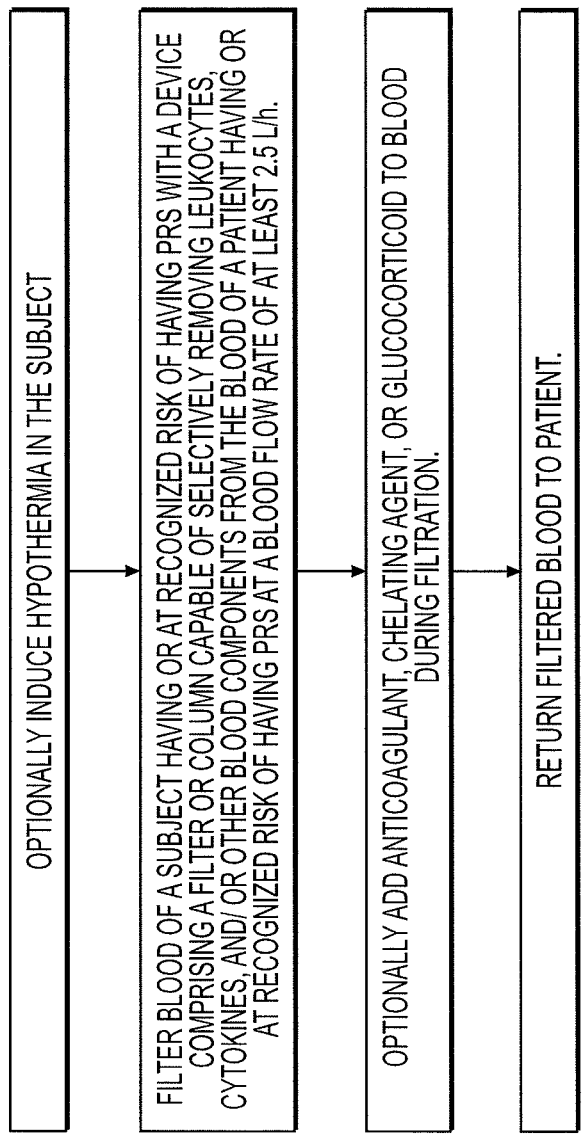
FIG. 7 shows a flow diagram for one possible course of treatment or prevention for post-resuscitation syndrome with a device capable of achieving a blood flow rate of at least 2.5 L/h.
Figure 8:
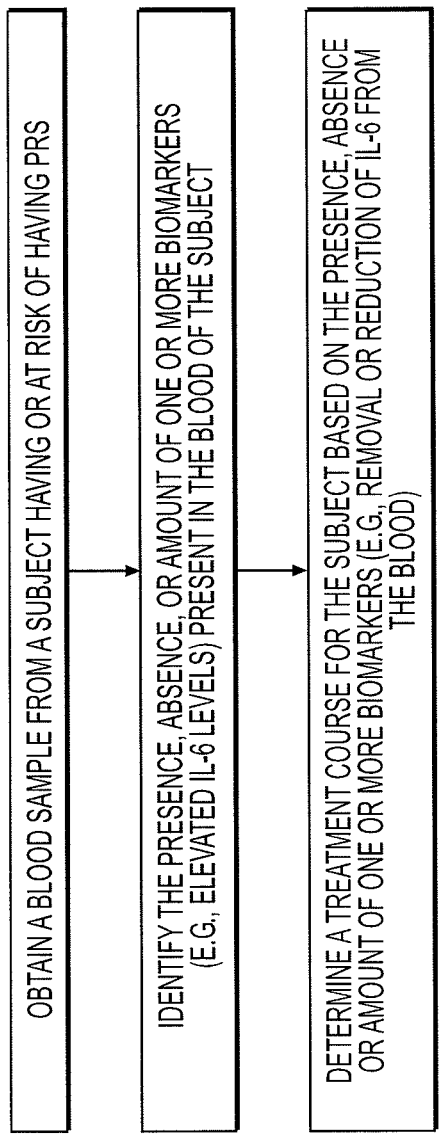
FIG. 8 shows a flow diagram for one possible method for determining a treatment course for post-resuscitation syndrome.

As used herein, the singular forms "a," "an," and "the" include the plural reference unless the context clearly dictates otherwise. For example, reference to "a cytokine" would also mean that mixtures of one or more cytokines can be present unless specifically excluded.

Except where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and claims are approximations that may vary depending upon the desired properties sought to be obtained by the present invention. At the very least, and not to be considered as an attempt to limit the application of the doctrine of equivalents to the scope of the claims, each numerical parameter should be construed in light of the number of significant digits and ordinary rounding conventions.

Additionally, the recitation of numerical ranges within this specification is considered to be a disclosure of all numerical values and ranges within that range. For example, if a range is from about 1 to about 50, it is deemed to include, for example, 1, 7, 34, 46.1, 23.7, or any other value or range within the range.

The various embodiments disclosed herein can be used separately and in various combinations unless specifically stated to the contrary.

Device

A device as invented by the inventors may comprise tubing, at least one pump, and a column or filter capable of selectively removing leukocytes, cytokines, and/or other blood components from the blood of a patient having or at recognized risk of having post-resuscitation syndrome (PRS) to effectively treat or prevent post-resuscitation syndrome. The device may be therapeutic and may function as a device to treat or prevent post-resuscitation syndrome and/or one or more symptoms of post-resuscitation syndrome. For example, the device may be capable of inducing hypothermia in a subject, pump and receive blood from a subject, pump blood from a subject through one or more filter modules, filter blood of a subject to remove toxic substances that cause or exacerbate post-resuscitation syndrome, and/or return the blood of a subject to the subject. The device may function to pump blood extracorporeally, for filtration, heating or cooling, or other treatment.

In another embodiment, there is provided a therapeutic device comprising tubing, at least one pump, a blood temperature regulator, and a column or filter, wherein the device is capable of detecting the presence and/or amount of soluble PRS-inducing or -exacerbating blood components, and selectively removing or partially removing one or more of the detected blood components from the blood of a subject.

In an embodiment, there is provided a therapeutic device comprising a pump, and a filtering module comprising one or more cylinders and filter material on at least a partial inner surface of the one or more cylinders, the therapeutic device being configured to send blood into and/or through the one or more cylinders along a spiral path such that blood components that induce or exacerbate PRS in a subject, or a portion thereof, are selectively retained in the one or more cylinders. In such a device, and without being bound to a particular mechanism of operation, centrifugal force is exerted on the blood sent into and/or through the one or more cylinders, such that one or more of the blood components that induce or exacerbate PRS in a subject contact the filter material. The device may, for example, slowly inject blood in an upward direction and simultaneously rotate the fluid contents to exert a centrifugal force on the blood sent into and/or through the one or more cylinders. In this way, the blood contacts the filter material on the inner surface of one or more cylinders and substances that induce or exacerbate PRS are selectively retained while the filtration product returns to the base of the filtration module via gravity, where it may be further circulated back to the subject. Such a device provides rapid and efficient removal and/or retention of selective blood components—even at high blood flow rates through the device. The centrifugal force within one or more cylinders of the device may be 10,000 to 100,000 G; 20,000-80,000 G, 25,000-75,000 G, or 50,000 G.

In another embodiment, there is provided a device comprising tubing, at least one pump, a blood temperature regulator, and a detachable module capable of removing leukocytes, cytokines, and/or other blood components from the blood of a patient to effectively treat or prevent post-resuscitation syndrome. There is also provided such a device, wherein the detachable module selectively removes cytokines up-regulated during post-resuscitation syndrome. There is also provided such a device wherein the detachable module selectively removes free iron radicals. There is also provided such a device wherein the detachable module may be exchanged or selected for insertion in the device depending upon the blood component to be removed. A cassette tubing system and slide stator pumps may be included and preparation time of the tubing may thereby be reduced. Arterial and venous tubing may be loaded simultaneously, and the use of cassette tubing allows for correct position of air detectors. The slide stator pumps also provide for tubing set up without winding.

A device as provided herein may be capable of therapeutic apheresis and/or continuous renal replacement therapy. The device may, for example, be capable of automated plasma recovery and/or may have pressure driven automatic flow control. The device may be capable of automatic priming and thereby reduced priming time compared to conventional devices. Reduced priming volumes and increased safety may also be achieved by automatic priming.

In an embodiment, the device may be high-volume hemofiltration device. The device may achieve blood flow rates of, for example, 1-400 mL/min. In a preferred embodiment, the device may be capable of blood flow rates of 200-400, 300-375, or 350 mL/min.

In an embodiment, the device is configured to increase flow rate through the filter or column when IL-6 plasma concentration levels, or when the levels of a different cytokine or blood component, are detected above 200 µg/L. The plasma concentration levels are not particularly limited. For example, if IL-6 plasma concentration levels in a subject are above 150-500 µg/L, the device may detect such concentration and adjust the flow rate through the filter or column accordingly. The device may also adjust flow rate through the filter or column to maintain plasma concentration levels of a PRS-inducing or -exacerbating blood component below a certain toxic threshold. For example, the device may be configured to adjust flow rate through the filter or column to maintain IL-6 plasma concentration levels below 150, 175, 190, 200, 210, or 250 µg/L in post-filtration blood.

Similarly, the timing of such detection and/or filtration/flow rate adjustment is not limited. The device may obtain measurements of blood component levels at any time, including, for example, 45 min, 50 min, 60 min, 65 min, 70 min, or 75 min after collecting a sample from the subject at risk of having or having post-resuscitation syndrome. The device may be further configured to detect levels of blood components such as cytokines, free radicals, etc., at intervals of 10 min, 15 min, 20 min, 30 min., 45 min, and so on.

The device of the present invention will be capable of a range of blood filtration rates as well. For example, the blood filtration rate of the device as described herein may achieve a blood filtration rate of 0.9 to 10 L/h, 1 to 9 L/h, 2 to 8 L/h, 2.5 to 5 L/h, 3, 4, 6, or 7 L/h.

In a preferred embodiment, the device may be configured for extracorporeal circulation. The device may be stationary or portable. The portable device may, for example, have wheels, and/or be of light weight and compact, such that it may be conveniently carried, transported, or rolled to a patient at risk of post-resuscitation syndrome.

Filters and Columns

The filter of the device is not particularly limited, and may be, for example, selected from commercially available filters, etc. The filter may be, for example, a leukocyte removing filter as described in U.S. Pat. Nos. 8,496,833; 7,641,794; and 7,655,146, each of which is incorporated by reference herein in its entirety. In an embodiment, the filter may be a surface treatment filter.

Similarly, the column of the device is not particularly limited, and may be a leukocytapheresis column or a commercially available column capable of removing leukocytes.

One of ordinary skill in the art will appreciate that the filter or column may be selected based on the nature and/or amount of blood components to be removed and/or reduced. Filters and columns of the invention may remove leukocytes, cytokines, and/or other blood components from the blood of a patient to effectively treat or prevent post-resuscitation syndrome. Leukocytes to be removed include, for example, granulocytes (e.g., neutrophils, eosinophils, or basophils), macrophages, monocytes, and/or lymphocytes (e.g., B cells and T cells). Filters and columns of the invention may remove all cells of a certain type or a partial amount. For example, the filters and/or columns of the invention may partially remove peripheral neutrophils from the blood of subject having or at risk of having PRS. Similarly, filters and columns of the invention may remove all cytokines of a certain type or just a partial amount or a percentage of one or more types of cytokine. Cytokines to be removed include any of the cytokines described herein. For example, the filter or column may be configured to reduce soluble IL-6 levels in the blood of a subject by 90%, 75%, 60%, 50%, 40%, etc.

The column or filter may also be configured to selectively remove free iron, free iron radicals, complement components, von Willebrand factor, free oxygen radicals, etc.

The column or filter may have a volume of 25-500 mL, 50-300 mL, 100-200 mL, 125-175 mL or 150 mL, and may be in the shape or a cylinder or cone. The column or filter may be 50-600 mm in height, 75-500 mm in height, 100-400 mm in height, 125-350 mm in height, 150-300 mm in height, 175-250 mm in height, 200-225 mm in height, 550, 450, or 375 mm in height. In an embodiment, the device may comprise multiple conical-shaped filters or membranes which selectively retain or exclude blood components based on size, binding capacity of the filter or membrane, or specificity with regard to, for example, cell type, protein charge, or amino acid sequence.

The column may be 10-220 mm, 20-200 mm, 30-180 mm, 40-160 mm, 50-150 mm, 75-100 mm, 60, 70, 80, 90, 110, 120, 130, 140, 170, or 190 mm in diameter.

The column or filter may comprise nonwoven fabric, such as nonwoven fabric comprising polyethylene terephthalate. In addition to polyethylene, other materials which may used as part of the column or filter include hydrogels, dextran (e.g., carboxymethyl dextran), cellulose, gold, or glass. The materials may be used alone or in combination. For example, the column or filter may comprise material capable of removing leukocytes and/or soluble blood components from the blood of a subject having or at recognized risk of having PRS at a blood flow rate through the filter of at least 2.5 L per hour to effectively treat or prevent PRS. The material may be such that is capable of, for example, selectively and simultaneously removing 1, 2, 3 or more blood components from the blood of a subject having or at recognized risk of having PRS at a blood flow rate through the filter of at least 1.0 L, 1.5 L, 2.0 L, 2.5 L, 3.0 L, 3.5 L, 4.0 L, 4.5 L, 5.0 L, 10 L or more per hour.

The column or filter may comprise an enhanced surface area or an enhanced area to dimension ratio. For example, a surface activated filtering agent present in the filter or column may enhance the chemical attraction of the filter or column material to one or more compounds. The surface area of the column or filter may be enhanced by nanofibers such as carbon nanofibers that are coupled to the surface. The high surface area, low density, and high pore volume of such nanofibers increase the functional filtration surface area of the column or filter. The surface area of the filter may also be enhanced by chemical vapor deposition (CVD). For example, a filter material such as carbon nanofibers may be exposed to chemical vapor deposition to yield nanofiber-supported nanoparticles. Alternatively, the surface area may be enhanced by nanoparticles sintered thereto by any process known to those of skill in the art. The blood components may be efficiently and selectively removed from the blood during filtering via such a column or filter having an enhanced surface area.

The column or filter may selectively remove inflammatory biomarkers from the blood. For example, the column or filter may be specifically adapted to selectively remove cytokines from whole blood, either by direct removal of IL-6 or by removal of cells that produce them. For example, the column or filter may be specifically adapted to selectively remove IL-6 from whole blood, either by direct removal of IL-6 or by removal of white blood cells that produce IL-6.

The column or filter may also be configured as a module. The module may be detachable. The column or filter may be present as part of a detachable filtration module or separately. In an embodiment, for example, a column for TNF-α may be detachable such that it may be removed from the device, and a filter or column for removing IL-6 may be inserted in its place. In this way, the detachable module may be exchanged or selected for insertion in the device depending upon the blood component or blood components to be removed.

In one aspect, the column or filter is capable of removing toxins and harmful substances associated with post-resuscitation syndrome, including, but not limited to: interleukins (e.g., IL-1β, IL-2, IL-4, IL-6, IL-10, and IL-15), tumor necrosis factor α (TNF-α), interferon (e.g., interferon-γ), c-reactive protein (CRP), nuclear factor-kappa B (NF-κB) subunit p65, elastase, inducible NO synthase (iNOS), heme oxygenase-1 (HO-1), free radicals (e.g., free iron radicals or free oxygen radicals), intracellular adhesion molecules (e.g., ICAM1, ICAM2, ICAM3, ICAM4, ICAM5), vascular cell adhesion molecule-1, complement components (e.g., terminal complement complex (TCC) or complement components C3a (C3a)), granulocyte-macrophage colony-stimulating factor (GM-CSF), monocyte chemoattractant protein-1 (MCP-1), Regulated on Activation, Normal T Cell Expressed and Secreted (RANTES) protein, and von Willibrand factor (VWF). The column or filter may also be configured to remove white blood cells (e.g., lymphocytes, macrophages, monocytes, granulocytes), or substances secreted by any such white blood cells, red blood cells, or platelets. In one embodiment, the filter module or column be configured to specifically remove one substance or molecule from the blood of a subject or configured to remove a combination of the above substances. In another embodiment, removal) of white blood cells may be performed to prevent an increase in the level of products produced or secreted by white blood cells.

The column, filter, and/or device of the instant invention may be sterilized by any number of methods, e.g., by gamma-ray sterilization, or by contacting the column, filter, and/or device with a sterilization agent, such as alcohol.

Other Device Components

The device may comprise one or more pumps. The pump may be any commercially available pump, for example, non-occlusive centrifugal pumps, slide stator pumps, etc. The pump may withdraw blood from the patient and transport it through the device. The invention provides, for example, a device comprising a pump that transports blood through an extracorporeal circuit or sub-circuit, or an infusion pump that delivers anticoagulants, liquid, solutes, substitute blood components, or other substances and compounds to blood. The one or more pumps of the device are not particularly limited. For example, the pump may be a belt-driven pump. The device may also include a syringe pump, stator pump, or other types of pumps suitable for methods as described herein. The pump may also be any pump that provides excellent stability from low to high speeds.

The tubing may be, for example, arterial and/or venous tubing. The tubing may be made of any suitable material including plastic or rubber.

The device may comprise a blood temperature regulator for activating a heater or cooler. The heater may be a resistance heater such as a wire coil. The heater may be in the form of a heat-generating surface. The cooler may be in the form of a heat-absorbing surface. The heat absorbing surface will generally comprise a metal foil wrapped around a catheter, typically having an exposed area of at least about 2 cm$^2$. In an embodiment, the cooler may be a thermoelectric cooler. The components of the device, including the blood temperature regulator, cooler, etc., may be configured to induce therapeutic hypothermia in a subject.

The device may comprise additional components or modules, such as an oxygenator, catheter, blood infuser, temperature sensor, etc. The oxygenator provides oxygenated blood to be returned to the patient's arterial system. The blood infuser may deliver large volumes of plasma substitute, blood substitute, or whole blood, optionally with preservation and or resuscitation cocktails.

In aspects and/or embodiments, the device may comprise one or more of an air-free pressure chamber, a pressure sensor, a blood leak detector, an air detector, a scale, an LED touch screen, and/or a battery. Among other functions the air-free pressure chamber may minimize contact between air and blood.

One or more of the components of the device may be heparin bonded.

A touch screen may display information relating to the nature and/or amount of one or more PRS-inducing or -exacerbating blood components in the blood to be filtered. The touch screen may display information related to, for example, IL-6 plasma concentration levels. The device of the present invention may also be configured to detect and display information about the nature and/or amount of the one or more PRS-inducing or -exacerbating blood components in the blood to be filtered within about 45 minutes, 30 minutes, 25 minutes, 20 minutes, 10 minutes, or less after filtration had started. A device as provided herein may be, for example, configured to detect and display information about the nature and/or amount of the one or more PRS-inducing or -exacerbating blood components in the blood to be filtered in 30 minute, 25 minute, 20 minute, 15 minute, 5 minutes, or 1 minutes intervals. A device as described herein may also adjust flow rates through the filter or column based on the information that is detected and displayed.

System

There is also provided a system for determining a treatment procedure for a subject having or at recognized risk of having PRS. The system may comprise one or more of the following: a module for obtaining a blood sample from the subject; a module for measuring and/or identifying the presence, absence, or amount of one or more biomarkers present in the blood of the subject after cardiac arrest, ischemia or other loss of circulation; a module and LED screen capable of determining and displaying a treatment procedure for the subject based on the presence, absence, or amount of the measured and/or identified one or more biomarkers; and an adjustable filter module. The system may be in the form of a kit or other assembly. The system may comprise device components as described herein, which components function in the context of the system to assist in effectively treating or preventing PRS.

Methods of Treatment and/or Prevention of Post-Resuscitation Syndrome

The invention provides methods of treating or preventing post-resuscitation syndrome comprising: passing the blood of a subject at risk of post-resuscitation syndrome through a therapeutic device configured to remove leukocytes, cytokines, free radicals, von Willibrand factor, and/or other blood components after cardiac arrest to effectively treat or prevent post-resuscitation syndrome.

The present invention also provides a method of treating or preventing PRS comprising filtering blood of a subject having or at recognized risk of having PRS with a device a described above.

There is also provided a method of treating or preventing post-resuscitation syndrome comprising inducing hypothermia in a subject at risk of post-resuscitation syndrome, and passing blood of the subject at risk of post-resuscitation syndrome through a device comprising tubing, at least one pump, a blood temperature regulator, and a column or filter, the device being capable of detecting the presence and/or amount of soluble PRS-inducing or -exacerbating blood components, and selectively removing or partially removing one or more of the detected blood components from the blood of a subject.

There is also provided a method of treating or preventing post-resuscitation syndrome comprising passing the blood of a subject at risk of post-resuscitation syndrome through a device configured to remove leukocytes, cytokines, free radicals, von Willibrand factor, and/or other blood components at a flow rate of at least 2.5 L per hour to effectively treat or prevent post-resuscitation syndrome.

Methods as described above may also include addition of an anticoagulant, a chelating agent, and/or a glucocorticoid to the blood as it passes through the device. The anticoagulant may be Anticoagulant Citrate Dextrose Solution A (ACD-A) or heparin.

Treatment methods may comprise filtering the blood of a subject having or at recognized risk of having PRS with a device comprising tubing, at least one pump, and a filter or column capable of selective removing leukocytes, cytokines, and/or other blood components from the blood of a patient having or at recognized risk of having PRS at a blood flow rate through the filter of at least 2.5 L per hour to effectively treat or prevent PRS. For example, the method may comprise filtering the blood extracorporeally to remove, for example, leukocytes. The leukocytes to be removed may be lymphocytes, granulocytes and/or monocytes. In an embodiment, the method comprises partial removal of leukocytes (e.g., lymphocytes or peripheral neutrophils), or partial removal of one or more cytokines (e.g., IL-4 or IL-6).

There is also provided a method of treating or preventing post-resuscitation syndrome comprising inducing hypothermia in a subject at risk of post-resuscitation syndrome, and passing blood of a subject at risk of post-resuscitation syndrome through a device as described above which includes a blood temperature regulator.

In one aspect of the invention, there is provided a method of treating children after extracorporeal circulation, e.g., for cardiac surgery.

In another aspect of the invention, there is provided a method of high-volume hemofiltration. High volume hemofiltration may be used to filter large quantities of blood rapidly. For example, high-volume hemofiltration may be used to achieve 100 L of fully balanced ultrafiltration over an 8-hour period. High volume hemofiltration may be performed, for example, at a rate of 180-220 ml/kg/h, 190-210 ml/kg/h, and preferably at 195-205 ml/kg/h. For example, high volume hemofiltration may be performed at 200 ml/kg/h for 8 hours. High volume hemofiltration may also be performed for 0.5-12 h, 1-10 h, 2-9 h, 3-8 h, 4-6 h, or for 5 h. There is also provided similar methods of high-volume ultrafiltration.

High volume hemofiltration may be performed with or without inducing hypothermia in the subject. Induction of hypothermia may control inflammatory processes and improve recovery and/or survival. Body temperature may be reduced to a desired temperature or range, e.g., 32-36° C., 33-35° C., or 34° C.

Timing of Treatment and/or Prevention

The timing and manner of treatment may vary depending upon several factors. Generally the sooner treatment begins after return of spontaneous circulation, the better the therapeutic prospects for the subject at risk of post-resuscitation syndrome. Treatment options and/or the substance to be filtered may also depend upon the timing of treatment. For example, treatment within 1 hour of cardiac arrest or cessation of circulatory function may comprise removal of white blood cells which secret toxic enzymes into the blood stream. Treatment within 24 h of cardiac arrest or cessation of circulatory function may comprise removal of one or more toxic enzymes and/or free radicals, which result from multifocal hypoxia and microcirculatory dysfunction that occur during this period. Treatment and/or prevention may begin, however, prior to cardiac arrest, ischemia, or similar event. Methods of treatment may also begin at 0 to 20 minutes, at 20 minutes to 6 hours, at 72 hours, etc., from return of spontaneous circulation (ROSC). When treatment methods include induction of hypothermia, body temperature is generally reduced soon after ischemia/surgery/loss of spontaneous circulation, e.g., within 1 hour, 45 minutes, 30 minutes, 25 minutes, 15 minutes or even 1 minute. When treatment methods include induction of hypothermia, body temperature reduction may also be induced upon return of spontaneous circulation, e.g., immediately after return of spontaneous circulation, within 0-5 minutes, 6-20 minutes, 21-45 minutes, or 46-60, or 90 minutes of return of spontaneous circulation. Hypothermia may be induced, for example, via infusion of cold saline, with ice bags, or by other conventional methods.

Duration and Manner of Administration

Treatments may be administered in a single session or in multiple sessions.

Subjects to be treated are not particularly limited. Subjects include patients who have experienced cardiac arrest, post-cardiac arrest brain injury, post-cardiac arrest myocardial dysfunction, systemic ischemia/reperfusion response, or persistent precipitating pathology such as cardiovascular disease, pulmonary disease, CNS disease, infection, hemorrhage, dehydration, etc. Subjects include any mammal having or at risk of having PRS, e.g., human subjects.

The blood circuit formed during the filtration process may be arterio-venous, whereby blood flows from an artery through a large bore cannula into tubing, proceeds through a filter, and returns from the filter to a vein. Alternatively, the blood circuit may be veno-venous such that blood flows from a vein to the filter and returns from the filter to a vein. Ultrafiltrate may collect in a filter jacket, drained through an ultrafiltrate line, discarded, and/or recycled either into the blood circuit or elsewhere. Blood flow may return to the patient at the wrist or radial artery or vein. Blood flow may also return to the patient at a femoral artery or vein access point, e.g., at the inner thigh near the groin.

Optional Induction of Hypothermia

The invention provides methods of treating or preventing post-resuscitation syndrome comprising optional induction of hypothermia in a subject. The induction of hypothermia may be therapeutic. The induction of hypothermia may, for example, be mild such that a patient's body temperature is reduced to, e.g., 33-36° C., moderate such that a patient's body temperature is reduced to, e.g., 28, 29, 30, 31, or 32° C., or deep such that a patient's body temperature is reduced to, e.g., below 28° C.

The particulars shown herein are by way of example and for purposes of illustrative discussion of embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description is taken with the drawings making apparent to those skilled in the art how the forms of the present invention may be embodied in practice.

The invention claimed is:

1. A therapeutic device for providing resuscitative treatment to a subject comprising tubing, at least one pump, a blood temperature regulator configured to induce therapeutic hypothermia in the subject, and a filter or column, the device being configured to form a single extracorporeal circuit, wherein:

the filter or column comprises a hydrogel layer to which one or more molecules capable of selectively binding one or more of the following soluble or secreted blood components has been immobilized: cytokines, inducible nitric oxide (NO) synthase, heme oxygenase-1, free radicals, intracellular adhesion molecules (ICAMs), vascular cell adhesion molecule-1, complement components, monocyte chemoattractant protein-1 (MCP-1), Regulated on Activation, Normal T Cell Expressed and Secreted (RANTES) protein, and von Willibrand factor (VWF); and the device is configured to (i) detect and display information on a screen provided thereon about the nature and/or amount of the one or more soluble or secreted blood components in the blood of the subject; (ii) pump blood received from the subject via the tubing through the filter or column at a blood flow rate of 4-24 L per hour; (iii) selectively remove one or more of the soluble or secreted blood components, or a portion thereof, from the blood of the subject; and (iii) return cooled blood to the subject to induce therapeutic hypothermia.

2. The therapeutic device of claim 1, which is configured to selectively remove one or more of interleukins (ILs), tumor necrosis factor α (TNF-α), c-reactive protein (CRP), nuclear factor-kappa B (NF-κB) subunit p65, interferon-γ, elastase, inducible NO synthase, heme oxygenase-1, free radicals, intracellular adhesion molecules, vascular cell adhesion molecule-1, complement components, granulocyte-macrophage colony-stimulating factor (GM-CSF), MCP-1, RANTES protein, and VWF from the blood of the subject.

3. The therapeutic device of claim 2, wherein the interleukins are IL-1β, IL-2, IL-4, IL-6, IL-10, and IL-15; the intracellular adhesion molecules are ICAM 1, ICAM2, ICAM3, ICAM4, and ICAM5; the free radicals are free iron radicals or free oxygen radicals; and the complement components are C3a or terminal complement complex (TCC).

4. The therapeutic device of claim 1, which is configured to selectively remove interleukin (IL-6).

5. The therapeutic device of claim 1, which is portable.

6. The therapeutic device of claim 1, which is configured for a blood filtration rate of 4-10 L/hr.

7. The therapeutic device of claim 1, wherein the hydrogel comprises dextran.

8. The therapeutic device according to claim 1, which is configured to adjust flow rate through the filter or column based on the information about the nature and/or amount of the one or more soluble or secreted blood components in the blood of the subject.

9. The therapeutic device of claim 1, which is configured for pressure-driven automatic flow control capable of adjusting flow rate through the filter or column to maintain the one or more soluble or secreted blood components in the blood of the subject below a toxicity threshold.

10. The therapeutic device of claim 1, which displays information relating to IL-6 plasma concentration levels.

11. The therapeutic device of claim 1, which is configured to detect and display information about the nature and/or amount of the one or more soluble or secreted blood components in the blood to be filtered in 30 minute intervals and to adjust flow rate through the filter or column based on the information.

12. The therapeutic device of claim 1, wherein the screen is an LED touch screen.

13. The therapeutic device of claim 8, which is configured to exert a centrifugal force within the filter or column sufficient to immobilize one or more of the soluble or secreted blood components, or a portion thereof, to the hydrogel layer.

14. The therapeutic device of claim 13, which is configured to detect IL-6 and adjust flow rate through the filter or column to maintain IL-6 below a toxicity threshold.

15. A therapeutic device for filtering blood comprising:
tubing;
a pump;
a blood temperature regulator configured to induce therapeutic hypothermia in a subject;
a filtering module comprising a base and one or more conical cylinders with the larger opening of the one or more cylinders oriented away from the base; and
filter material on at least a partial inner surface of the one or more cylinders, the filter material comprising a hydrogel layer to which one or more molecules capable of selectively binding one or more soluble or secreted blood components has been attached,
the therapeutic device being configured to exert a centrifugal force on the blood within the one or more cylinders, thereby sending the blood into or through the one or more cylinders along a spiral path such that the soluble or secreted blood components, or a portion thereof, are selectively retained in the one or more cylinders,
wherein the soluble or secreted blood components comprise one or more of cytokines, inducible nitric oxide (NO) synthase, heme oxygenase-1, free radicals, intracellular adhesion molecules (ICAMs), vascular cell adhesion molecule-1, complement components, monocyte chemoattractant protein-1 (MCP-1), Regulated on Activation, Normal T Cell Expressed and Secreted (RANTES) protein, and von Willibrand factor (VWF), and
wherein the tubing, the blood temperature regulator, the pump, and the filtering module are configured to form an extracorporeal circuit that pumps blood from the subject via the tubing through the filtering module and returns cooled blood to the subject to induce therapeutic hypothermia.

16. The therapeutic device of claim 15, configured to obtain a centrifugal force within the one or more cylinders of 10,000 to 100,000 G.

17. The therapeutic device of claim 15, which comprises more than one conical cylinder.

18. A therapeutic device for filtering blood comprising:
a filtering module configured to selectively remove one or more soluble or secreted blood components that induce or exacerbate post-resuscitation syndrome (PRS), or a portion thereof, in a subject, and comprising a hydrogel layer to which one or more molecules capable of selectively binding one or more of the soluble or secreted blood components has been immobilized;
a pump and tubing for pumping blood from a subject through the filtering module at a rate of 4-24 L/hr and back to the subject;
a module capable of measuring and/or identifying the presence, absence, or amount of the one or more soluble or secreted blood components;
a touch screen that displays information relating to the nature and/or amount of one or more of the soluble or secreted blood components; and
a blood temperature regulator configured to induce therapeutic hypothermia in the subject;
wherein the one or more soluble or secreted blood components, or a portion thereof, comprise one or more of cytokines, inducible nitric oxide (NO) synthase, heme oxygenase-1, free radicals, intracellular adhesion molecules (ICAMs), vascular cell adhesion molecule-1, complement components, monocyte chemoattractant protein-1 (MCP-1), Regulated on Activation, Normal T Cell Expressed and Secreted (RANTES) protein, and von Willibrand factor (VWF), and wherein the device is further configured for pressure-driven automatic flow control capable of adjusting flow rate through the filtering module based on the information about the nature and/or amount of the one or more soluble or secreted blood components in the blood of the subject.

19. The therapeutic device according to claim 18, wherein the touch screen is an LED touch screen.

20. The therapeutic device of claim 18, wherein the filtering module is capable of removing one or more of interleukins (ILs), tumor necrosis factor α (TNF-α), c-reactive protein (CRP), nuclear factor-kappa B (NF-κB) subunit p65, interferon-γ, elastase, inducible NO synthase, heme oxygenase-1, free radicals, intracellular adhesion molecules, vascular cell adhesion molecule-1, complement components, granulocyte-macrophage colony-stimulating factor (GM-CSF), MCP-1, RANTES protein, and VWF.

21. The therapeutic device of claim 20, wherein the interleukins are IL-1β, IL-2, IL-4, IL-6, IL-10, and IL-15; the intracellular adhesion molecules are ICAM1, ICAM2, ICAM3, ICAM4, and ICAM5; the free radicals are free iron radicals or free oxygen radicals; and the complement components are C3a or terminal complement complex (TCC).

22. The therapeutic device of claim 21, which is configured to detect IL-6 and adjust flow rate through the filter or column to maintain IL-6 below a toxicity threshold.

23. The therapeutic device of claim 21, which is configured for a blood filtration rate of 4-10 L/hr.

24. A method of treating or preventing Post-Resuscitation Syndrome (PRS) comprising:

filtering blood of a subject having or at recognized risk of having PRS with the device of claim 1.

* * * * *